United States Patent
Satoh (10) Patent No.: US 8,303,506 B2
(45) Date of Patent: Nov. 6, 2012

(54) ULTRASONIC DIAGNOSTIC APPARATUS AND ULTRASONIC IMAGING METHOD AND PROGRAM

(75) Inventor: Yoshiaki Satoh, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 718 days.

(21) Appl. No.: 12/483,565

(22) Filed: Jun. 12, 2009

(65) Prior Publication Data

US 2009/0312642 A1    Dec. 17, 2009

(30) Foreign Application Priority Data

Jun. 17, 2008   (JP) ................................. 2008-157406

(51) Int. Cl.
*A61B 8/14* (2006.01)

(52) U.S. Cl. .................. 600/447; 600/443; 600/437

(58) Field of Classification Search .................. 600/437, 600/443, 447
See application file for complete search history.

(56) References Cited

U.S. PATENT DOCUMENTS 3,881,466 A * 5/1975 Wilcox ........................... 73/626
4,159,462 A * 6/1979 Rocha et al. ................... 367/97

FOREIGN PATENT DOCUMENTS

JP            07-327986 A    12/1995
JP         2000-333951 A    12/2000

* cited by examiner

*Primary Examiner* — Long V. Le
*Assistant Examiner* — Farshad Negarestan
(74) *Attorney, Agent, or Firm* — Sughrue Mion, PLLC (57) ABSTRACT

An ultrasonic diagnostic apparatus in which one of an imaging method with advantageous time resolution and an imaging method with advantageous spatial resolution can be selectively used according to an imaging object. The apparatus includes a transmission control unit for controlling a drive signal generating unit to scan the object while shifting a center position of a group of transducers, which simultaneously transmit ultrasonic waves, by a distance not larger than an interval of plural transducers in a first imaging mode and shifting a center position of a group of transducers, which simultaneously transmit ultrasonic waves, by a distance not less than twice the interval in a second imaging mode, and an image generating unit for generating an image signal at a first frame rate in the first imaging mode and a second frame rate higher than the first frame rate in the second imaging mode.

27 Claims, 8 Drawing Sheets

NUMBER OF TIMES OF TRANSMISSION: 1

FIG.2B

NUMBER OF TIMES OF TRANSMISSION: 2

FIG.2C

NUMBER OF TIMES OF TRANSMISSION: N

FIG.5A
NUMBER OF TIMES OF TRANSMISSION: 1

FIG.5B
NUMBER OF TIMES OF TRANSMISSION: 2

FIG.5C
NUMBER OF TIMES OF TRANSMISSION: M

NUMBER OF TIMES OF TRANSMISSION: 1

FIG. 7B

NUMBER OF TIMES OF TRANSMISSION: 2

FIG. 7C

NUMBER OF TIMES OF TRANSMISSION: M'

ULTRASONIC DIAGNOSTIC APPARATUS AND ULTRASONIC IMAGING METHOD AND PROGRAM

CROSS-REFERENCE TO RELATED APPLICATION

The present application claims priority from Japanese Patent Application No. 2008-157406 filed on Jun. 17, 2008, the contents of which are incorporated herein by reference in their entirety.

BACKGROUND OF THE INVENTION

1. Field of the Invention

The present invention relates to an ultrasonic diagnostic apparatus for imaging organs and so on within a living body by transmitting and receiving ultrasonic waves to generate ultrasonic images to be used for diagnoses. Further, the present invention relates to an ultrasonic imaging method and ultrasonic imaging program to be used in the ultrasonic diagnostic apparatus.

2. Description of a Related Art

In medical fields, various imaging technologies have been developed for observation and diagnoses within an object to be inspected. Especially, ultrasonic imaging for acquiring interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in obstetrics but also gynecology, circulatory system, digestive system, and so on.

Generally, in an ultrasonic diagnostic apparatus, an ultrasonic probe including plural ultrasonic transducers having transmission and reception functions of ultrasonic waves is used. Using such an ultrasonic probe, an object to be inspected is scanned by ultrasonic waves transmitted from the plural ultrasonic transducers, ultrasonic echoes reflected within the object are received and reception focusing processing is performed, and thereby, image information on structures (e.g., internal organs, diseased tissues, and so on) existing within the object can be obtained based on intensity of the ultrasonic echoes.

In ultrasonic imaging, it is constantly required that the balance between improvements in time resolution and improvements in spatial resolution is achieved. Especially, in the case of an ultrasonic examination of heart, high time resolution is required for observation of motion of heart wall moving at a high speed. On the other hand, in the case of an ultrasonic examination of abdomen, the structure of a tissue part is often observed in detail, and high spatial resolution is required. However, when the sound ray density is increased for higher spatial resolution, it becomes difficult to maintain the conventional frame rate.

As related technologies, Japanese Patent Application Publication JP-P2000-333951A discloses an ultrasonic imaging apparatus intended for achieving the balance between improvements in time resolution of imaging and improvements in spatial resolution of images. The ultrasonic imaging apparatus includes ultrasonic transmitting means for transmitting ultrasonic waves, reception signal forming means for forming reception signals based on echoes of the transmitted ultrasonic waves, image generating means for generating an image based on the formed reception signals, and image display means for displaying the generated image, and the ultrasonic transmitting means performs scanning of ultrasonic beam in the sound ray sequence within an imaging range by using sound rays interlaced with the sound rays at the previous scanning. According to JP-P2000-333951A, scanning the object by interlace method improves the apparent spatial resolution, but cannot improve the time resolution.

Further, Japanese Patent Application Publication JP-A-7-327986 discloses an ultrasonic image processing apparatus intended for preventing the reduction of frame rate. The ultrasonic image processing apparatus includes an ultrasonic probe segmented into plural groups according to a predetermined rule, transmitting and receiving means for transmitting and receiving waves for the respective segmented groups of the ultrasonic probe, phase-matching and adding means for phase-matching and adding echo data of all elements used for receiving waves with respect to each transmission and reception, storage means for storing data added by the phase-matching and adding means, and aperture synthesizing means for synthesizing apertures to obtain an ultrasonic image when transmission and reception of waves are performed for the number of the segments and all echo data are stored in the storage means. However, in the method of scanning the object by simultaneously transmitting plural ultrasonic beams, the influence of crosstalk cannot sufficiently be eliminated and it is difficult to sufficiently improve the spatial resolution.

SUMMARY OF THE INVENTION

The present invention has been achieved in view of the above-mentioned problems. A purpose of the present invention is to provide an ultrasonic diagnostic apparatus in which one of an imaging method with advantageous time resolution and an imaging method with advantageous spatial resolution can be selectively used according to an object of imaging or the like. A further purpose of the present invention is to provide an ultrasonic imaging method and ultrasonic imaging program to be used in the ultrasonic diagnostic apparatus.

In order to accomplish the above-mentioned purposes, an ultrasonic diagnostic apparatus according to one aspect of the present invention includes: an ultrasonic probe including plural ultrasonic transducers for transmitting ultrasonic waves to an object to be inspected according to drive signals and receiving ultrasonic echoes propagating from the object to output reception signals; a drive signal generating unit for supplying the drive signals to the plural ultrasonic transducers, respectively; a reception signal processing unit for processing the reception signals outputted from the plural ultrasonic transducers, respectively; control means for setting one of a first imaging mode and a second imaging mode; transmission control means for controlling the drive signal generating unit to scan the object while shifting a center position of a group of ultrasonic transducers, which simultaneously transmit ultrasonic waves, by a distance not larger than an interval of the plural ultrasonic transducers in the first imaging mode, and controlling the drive signal generating unit to scan the object while shifting a center position of a group of ultrasonic transducers, which simultaneously transmit ultrasonic waves, by a distance not less than twice the interval of the plural ultrasonic transducers in the second imaging mode; and image generating means for generating an image signal at a first frame rate in the first imaging mode based on the reception signals outputted from the reception signal processing unit, and generating an image signal at a second frame rate higher than the first frame rate in the second imaging mode based on the reception signals outputted from the reception signal processing unit.

Further, an ultrasonic imaging method according to one aspect of the present invention is an ultrasonic imaging method to be used in an ultrasonic diagnostic apparatus having an ultrasonic probe including plural ultrasonic transducers for transmitting ultrasonic waves to an object to be inspected according to drive signals and receiving ultrasonic echoes propagating from the object to output reception signals, a drive signal generating unit for supplying the drive signals to the plural ultrasonic transducers, respectively, and a reception signal processing unit for processing the reception signals outputted from the plural ultrasonic transducers, respectively, and the method includes the steps of: (a) setting one of a first imaging mode and a second imaging mode; (b) controlling the drive signal generating unit to scan the object while shifting a center position of a group of ultrasonic transducers, which simultaneously transmit ultrasonic waves, by a distance not larger than an interval of the plural ultrasonic transducers in the first imaging mode, and generating an image signal at a first frame rate in the first imaging mode based on the reception signals outputted from the reception signal processing unit; and (c) controlling the drive signal generating unit to scan the object while shifting a center position of a group of ultrasonic transducers, which simultaneously transmit ultrasonic waves, by a distance not less than twice the interval of the plural ultrasonic transducers in the second imaging mode, and generating an image signal at a second frame rate higher than the first frame rate in the second imaging mode based on the reception signals outputted from the reception signal processing unit.

Furthermore, an ultrasonic imaging program according to one aspect of the present invention is an ultrasonic imaging program to be used in an ultrasonic diagnostic apparatus having an ultrasonic probe including plural ultrasonic transducers for transmitting ultrasonic waves to an object to be inspected according to drive signals and receiving ultrasonic echoes propagating from the object to output reception signals, a drive signal generating unit for supplying the drive signals to the plural ultrasonic transducers, respectively, and a reception signal processing unit for processing the reception signals outputted from the plural ultrasonic transducers, respectively, and the program is embodied on a computer readable medium and allows a CPU to execute the procedures of: (a) setting one of a first imaging mode and a second imaging mode; (b) controlling the drive signal generating unit to scan the object while shifting a center position of a group of ultrasonic transducers, which simultaneously transmit ultrasonic waves, by a distance not larger than an interval of the plural ultrasonic transducers in the first imaging mode, and generating an image signal at a first frame rate in the first imaging mode based on the reception signals outputted from the reception signal processing unit; and (c) controlling the drive signal generating unit to scan the object while shifting a center position of a group of ultrasonic transducers, which simultaneously transmit ultrasonic waves, by a distance not less than twice the interval of the plural ultrasonic transducers in the second imaging mode, and generating an image signal at a second frame rate higher than the first frame rate in the second imaging mode based on the reception signals outputted from the reception signal processing unit.

According to the one aspect of the present invention, by generating an image signal at the first frame rate while line-sequentially imaging the object in the first imaging mode and generating an image signal at the second frame rate while frame-sequentially imaging the object in the second imaging mode, one of an imaging method with advantageous time resolution and an imaging method with advantageous spatial resolution can be selectively used according to an object of imaging or the like.

DESCRIPTION OF THE PREFERRED EMBODIMENTS

Hereinafter, embodiments of the present invention will be explained in detail with reference to the drawings.

Figure 1:
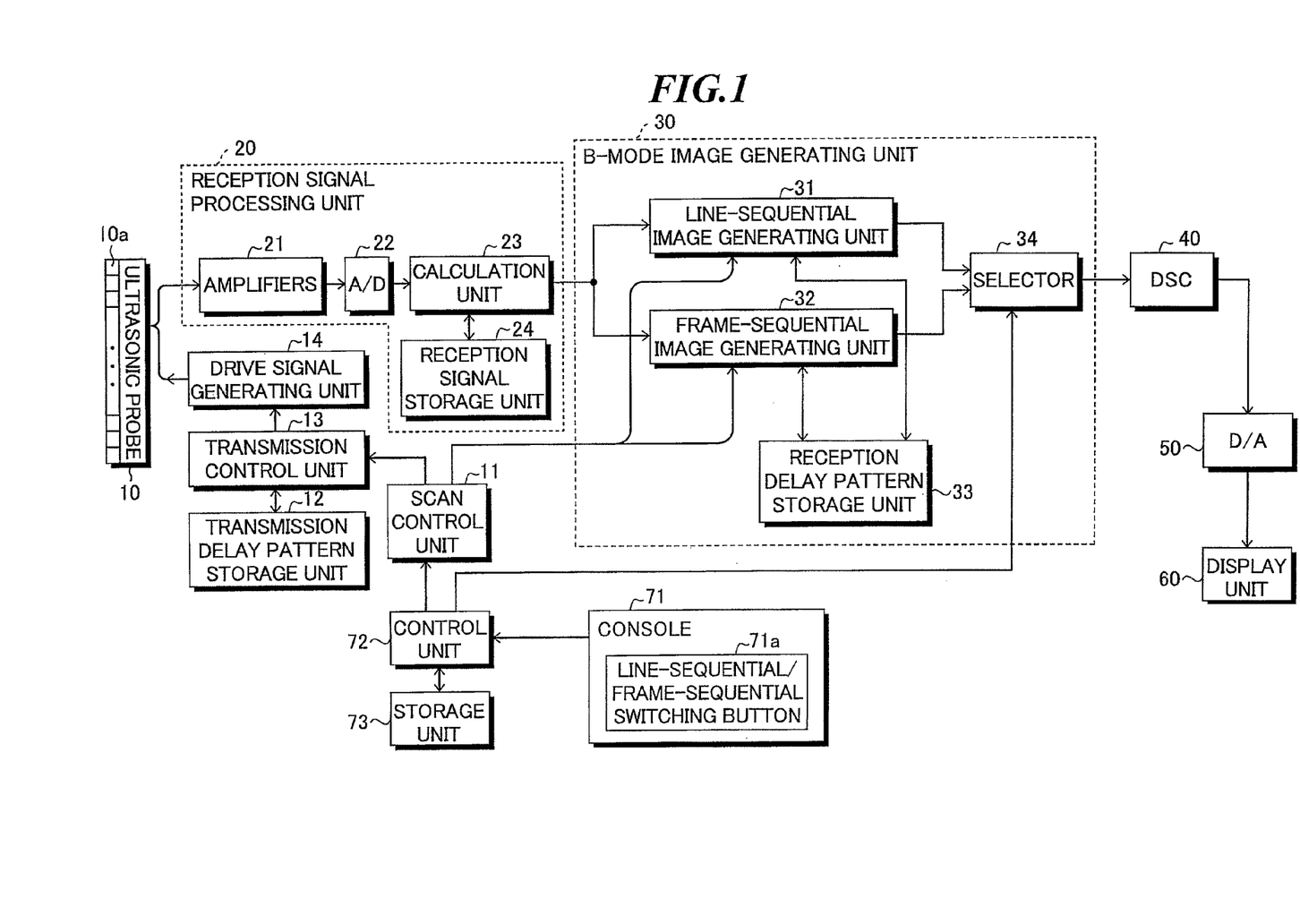
FIG. 1 is a block diagram showing a configuration of an ultrasonic diagnostic apparatus according to one embodiment of the present invention.

FIG. 1 is a block diagram showing a configuration of an ultrasonic diagnostic apparatus according to one embodiment of the present invention. The ultrasonic diagnostic apparatus includes an ultrasonic probe 10, a scan control unit 11, a transmission delay pattern storage unit 12, a transmission control unit 13, a drive signal generating unit 14, a reception signal processing unit 20, a B-mode image generating unit 30, a DSC (digital scan converter) 40, a D/A converter 50, a display unit 60, a console 71, a control unit 72, and a storage unit 73.

The ultrasonic probe 10 may be an external probe of linear scan type, convex scan type, sector scan type, or the like, or a probe for ultrasonic endoscope of electronic radial scan type or the like. The ultrasonic probe 10 includes plural ultrasonic transducers 10a forming a one-dimensional or two-dimensional transducer array. These ultrasonic transducers 10a transmit ultrasonic waves based on applied drive signals, and receive propagating ultrasonic echoes to output reception signals.

Each ultrasonic transducer includes a vibrator having electrodes formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like. When a pulsed or continuous wave voltage is applied to the electrodes of the vibrator, the piezoelectric material expands and contracts. By the expansion and contraction, pulse or continuous wave ultrasonic waves are generated from the respective vibrators, and an ultrasonic beam is formed by synthesizing these ultrasonic waves. Further, the respective vibrators expand and contract by receiving the propagating ultrasonic waves and generate electric signals. These electric signals are outputted as reception signals of ultrasonic waves.

The scan control unit 11 sequentially sets the transmission directions of ultrasonic beams and the reception directions of ultrasonic echoes. The transmission delay pattern storage unit 12 has stored plural transmission delay patterns to be used when the ultrasonic beam is formed. The transmission control unit 13 selects one transmission delay pattern from among the plural transmission delay patterns stored in the transmission delay pattern storage unit 12 according to the transmission direction set by the scan control unit 11, and sets delay times to be provided to drive signals for a selected group of ultrasonic transducers based on the selected transmission delay pattern. Alternatively, the transmission control unit 13 may set delay times such that the ultrasonic waves transmitted at a time from the selected group of ultrasonic transducers reach the corresponding imaging region within the object.

The drive signal generating unit 14 includes plural pulsers corresponding to the plural ultrasonic transducers 10a, for example. The drive signal generating unit 14 supplies drive signals to the ultrasonic probe 10 according to the delay times set by the transmission control unit 13 such that the ultrasonic waves transmitted from the selected group of ultrasonic transducers form an ultrasonic beam, or supplies drive signals to the ultrasonic probe 10 such that the ultrasonic waves transmitted at a time from the selected group of ultrasonic transducers reach the entire corresponding imaging region within the object.

In the embodiment, (i) a first imaging mode (referred to as "line-sequential imaging mode" in this application) of scanning the object while shifting a center position of a group of ultrasonic transducers, which simultaneously transmit ultrasonic waves, by a distance not larger than an interval of the plural ultrasonic transducers, and (ii) a second imaging mode (referred to as "frame-sequential imaging mode" in this application) of scanning the object while shifting a center position of a group of ultrasonic transducers, which simultaneously transmit ultrasonic waves, by a distance not less than twice the interval of the plural ultrasonic transducers are used.

The reception signal processing unit 20 includes plural preamplifiers 21 and plural A/D converters 22 corresponding to the plural ultrasonic transducers 10a. The reception signals outputted from the plural ultrasonic transducers 10a are amplified in the amplifiers 21, and the analog reception signals outputted from the amplifiers 21 are converted into digital reception signals by the A/D converters 22.

Further, the reception signal processing unit 20 includes calculation unit 23 and reception signal storage unit 24. Under the control of the scan control unit 11, the calculation unit 23 sequentially stores the reception signals outputted from the A/D converters 22 in the reception signal storage unit 24, and according to need, performs calculation processing of adding or averaging of the reception signals stored in the reception signal storage unit 24, and then, supplies calculation result to the B-mode image generating unit 30. Incidentally, the calculation unit 23 can also supply the reception signals outputted from the A/D converters 22 to the B-mode image generating unit 30 without calculation.

The B-mode image generating unit 30 generates a B-mode image signal as tomographic image information on tissues within the object based on the reception signals outputted from the reception signal processing unit 20. The B-mode image generating unit 30 includes a line-sequential image generating unit 31, a frame-sequential image generating unit 32, a reception delay pattern storage unit 33, and a selector 34. The reception delay pattern storage unit 33 has stored plural reception delay patterns to be used when reception focusing processing is performed on the reception signals outputted from the plural ultrasonic transducers 10a.

In the line-sequential imaging mode, the line-sequential image generating unit 31 selects one reception delay pattern from among the plural reception delay patterns stored in the reception delay pattern storage unit 33 according to the reception direction set by the scan control unit 11, and performs reception focusing processing by providing delays to the reception signals based on the selected reception delay pattern and adding the reception signals to one another. By the reception focusing processing, sound ray signals in which the focus of the ultrasonic echoes is narrowed are formed. Further, the line-sequential image generating unit 31 performs envelope detection processing on the formed sound ray signals to generate an image signal at a first frame rate.

In the frame-sequential imaging mode, the frame-sequential image generating unit 32 selects one reception delay pattern from among the plural reception delay patterns stored in the reception delay pattern storage unit 33 according to the reception direction set by the scan control unit 11, and performs reception focusing processing by providing delays to the reception signals based on the selected reception delay pattern and adding the reception signals to one another. By the reception focusing processing, sound ray signals in which the focus of the ultrasonic echoes is narrowed are formed. Further, the frame-sequential image generating unit 32 performs envelope detection processing on the formed sound ray signals to generate an image signal at a second frame rate higher than the first frame rate.

The selector 34 selects either one of the image signal generated by the line-sequential image generating unit 31 and the image signal generated by the frame-sequential image generating unit 32 under the control of the control unit 72. The DSC 40 converts (raster-converts) the image signal selected by the selector 34 into an image signal that follow the normal scan system of television signals and performs necessary image processing such as gradation processing to generate an image signal for display.

The D/A converter 50 converts the digital image signal outputted from the DSC 40 into an analog image signal. The display unit 60 includes a display device such as a CRT, LCD, or the like, and displays ultrasonic images based on the analog image signal.

The console 71 is used when an operator inputs various commands. The console 71 includes a line-sequential/frame-sequential switching button 71a. The operator can switch between the line-sequential imaging mode and the frame-sequential imaging mode by pressing down the line-sequential/frame-sequential switching button 71a.

The control unit 72 controls the scan control unit 11, selector 34, and so on according to the operation of the operator using the console 71. Further, the control unit 72 stores information on the imaging mode in connection with the image signal in the storage unit 73 in response to a command for saving the image signal.

In the embodiment, the scan control unit 11, transmission control unit 13, the calculation unit 23, B-mode image generating unit 30, DSC 40, and control unit 72 are formed of a CPU and software (ultrasonic imaging program), however, they may be formed by digital circuits or analog circuits. The software is stored in the storage unit 73. As a recording medium in the storage unit 73, not only a built-in hard disk but also a flexible disk, MO, MT, RAM, CD-ROM, DVD-ROM, or the like may be used.

Next, an operation of the ultrasonic diagnostic apparatus as shown in FIG. 1 will be explained.

Figure 2A:
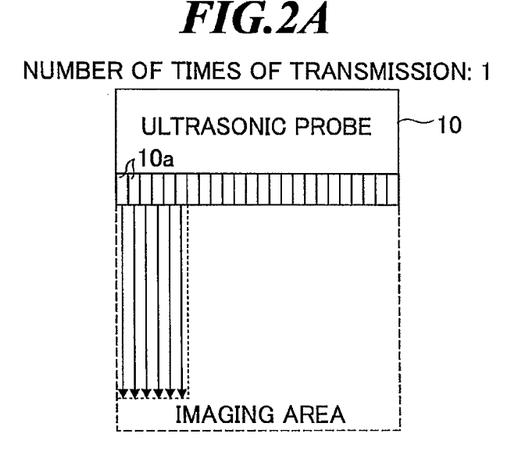
FIGS. 2A-2C are diagrams for explanation of transmission operation in a line-sequential imaging mode.
Figure 2B:
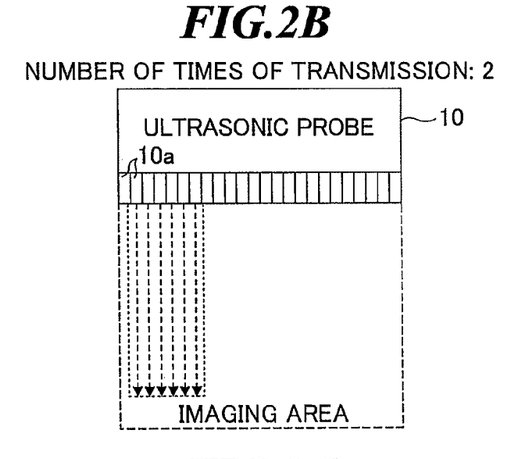
Figure 2C:
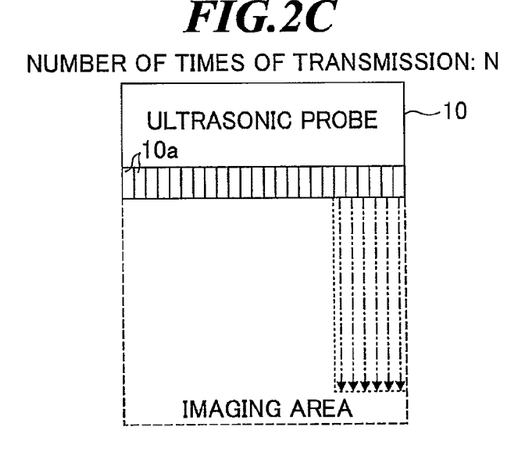

FIGS. 2A-2C are diagrams for explanation of transmission operation in the line-sequential imaging mode. As shown in FIG. 2A, drive signals are supplied to a group of ultrasonic transducers selected from among the plural ultrasonic transducers 10a included in the ultrasonic probe 10, and the selected group of ultrasonic transducers simultaneously transmit ultrasonic waves. Here, an ultrasonic beam may be formed by shifting phases of the ultrasonic waves to be simultaneously transmitted from the selected group of ultrasonic transducers, or phases of the ultrasonic waves to be simultaneously transmitted from the selected group of ultrasonic transducers may be made the same.

Then, as shown in FIG. 2B, a group of ultrasonic transducers for simultaneously transmitting ultrasonic waves is shifted one by one, and thereby, the object is scanned. That is, a center position of a group of ultrasonic transducers, which simultaneously transmits ultrasonic waves, is shifted by a distance equal to an interval of the plural ultrasonic transducers 10a. Then, as shown in FIG. 2C, after the N times of transmission, scanning of the entire imaging area is completed. In the line-sequential imaging mode, in the case where transmission focusing processing is performed, N imaging lines are sequentially formed by N times of transmission operation in one frame period.

Figure 3:
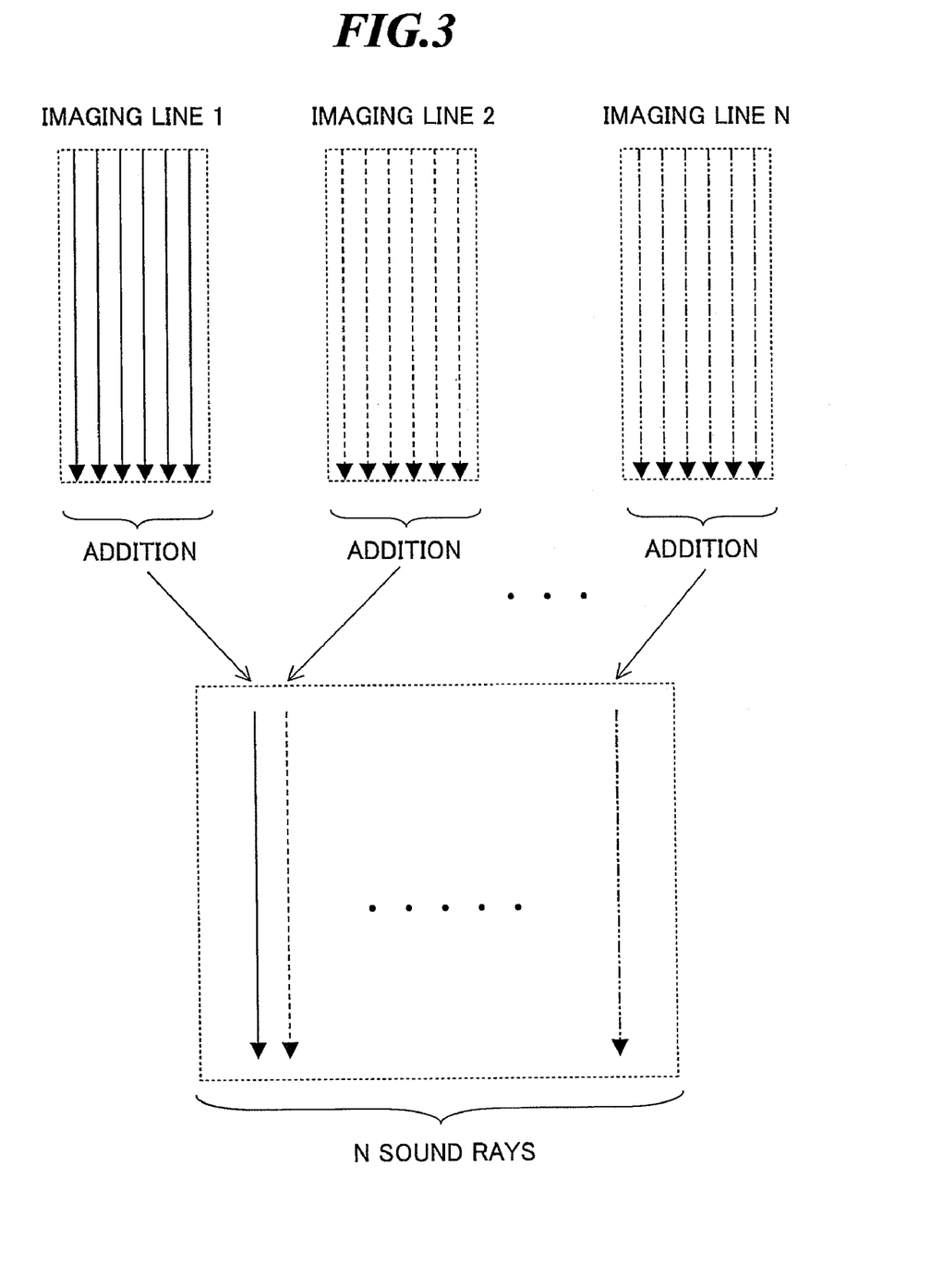
FIG. 3 is a diagram for explanation of a reception operation in the line-sequential imaging mode.

FIG. 3 is a diagram for explanation of a reception operation in the line-sequential imaging mode. As shown in FIG. 3, reception signals obtained by a selected group of ultrasonic transducers receiving ultrasonic echoes corresponding to one imaging line are phase-matched and added to one another, and thereby, a sound ray signal corresponding to one sound ray is obtained. By repeating this operation with respect to N imaging lines, sound ray signals corresponding to N sound rays are obtained in one frame period.

Alternatively, a center position of a group of ultrasonic transducers, which simultaneously transmits ultrasonic waves, may be shifted by a distance less than an interval of the plural ultrasonic transducers 10a. This is realized by changing a number of ultrasonic transducers, which simultaneously transmits ultrasonic waves, at every imaging line, or providing a minute angle displacement to a transmission beam at every imaging line. The former case will be explained as follows.

Figure 4:
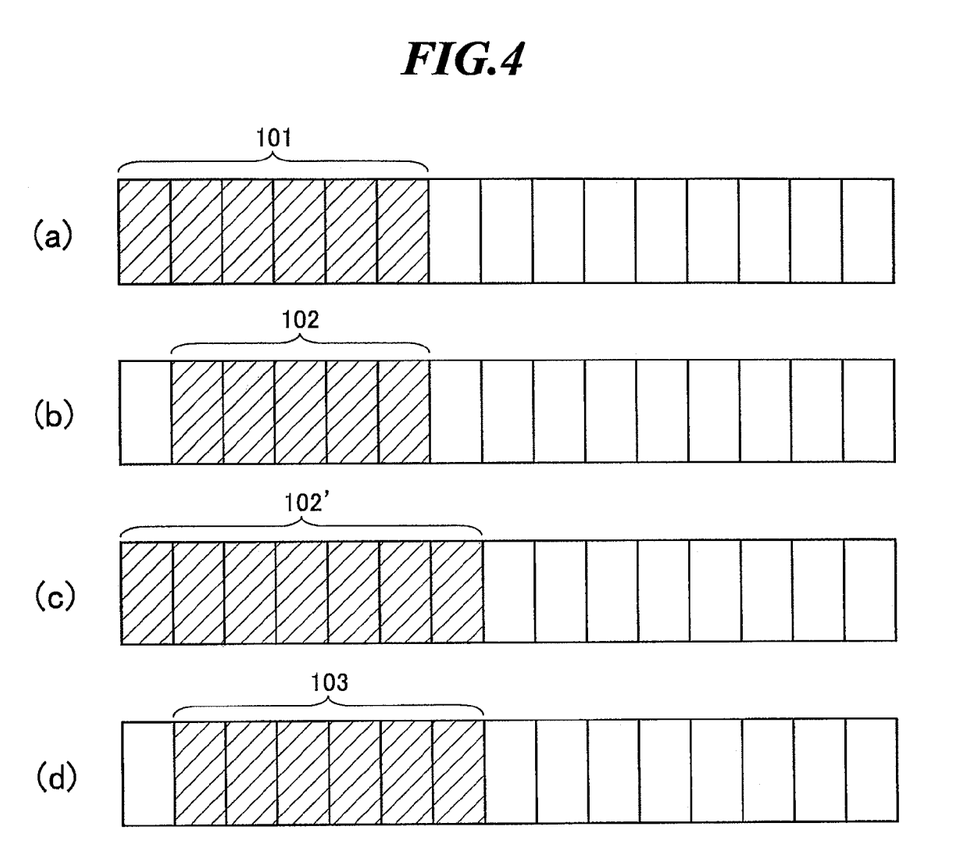
FIG. 4 is a diagram showing shifts of a group of ultrasonic transducers which simultaneously transmit ultrasonic waves.

FIG. 4 is a diagram showing shifts of a group of ultrasonic transducers which simultaneously transmit ultrasonic waves. FIG. 4 shows plural ultrasonic transducers arranged at a predetermined interval in an azimuth direction. And among the plural ultrasonic transducers, ultrasonic transducers which transmit ultrasonic waves are shown by hatching. Further, it is assumed that an ultrasonic transducer (hereinafter, also referred to as "element") is numbered from a left end in the drawing.

At a first time transmission, as shown in FIG. 4(a), a first group 101 including first to sixth elements are used to simultaneously transmit ultrasonic waves. At a second time transmission, as shown in FIG. 4(b), a second group 102 including second to sixth elements are used to simultaneously transmit ultrasonic waves. In this example, a center position of a group of elements, which simultaneously transmit ultrasonic waves, is shifted by 0.5 times the element interval.

Alternatively, instead of FIG. 4(b), a group of elements may be shifted as shown in FIG. 4(c). At a second time transmission, as shown in FIG. 4(c), a second group 102' including first to seventh elements are used to simultaneously transmit ultrasonic waves. Also in this example, a center position of a group of elements, which simultaneously transmit ultrasonic waves, is shifted by 0.5 times the element interval.

At a third time transmission, as shown in FIG. 4(d), a third group 103 including second to seventh elements are used to simultaneously transmit ultrasonic waves. In this example, a center position of a group of elements, which simultaneously transmit ultrasonic waves, is shifted by 0.5 times the element interval in comparison with FIG. 4(b) or (c).

Figure 5A:
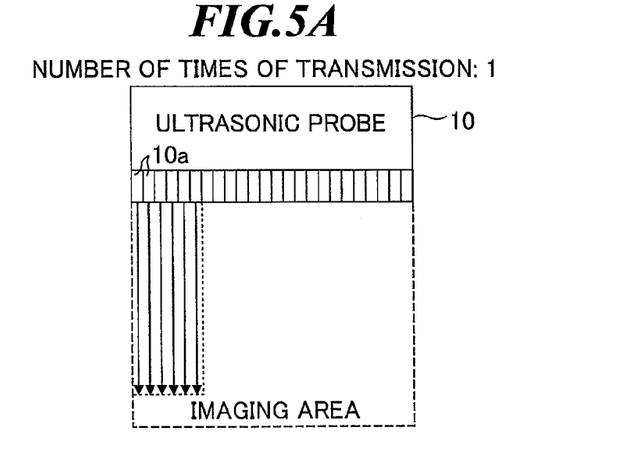
FIGS. 5A-5C are diagrams for explanation of transmission operation in a frame-sequential imaging mode.
Figure 5B:
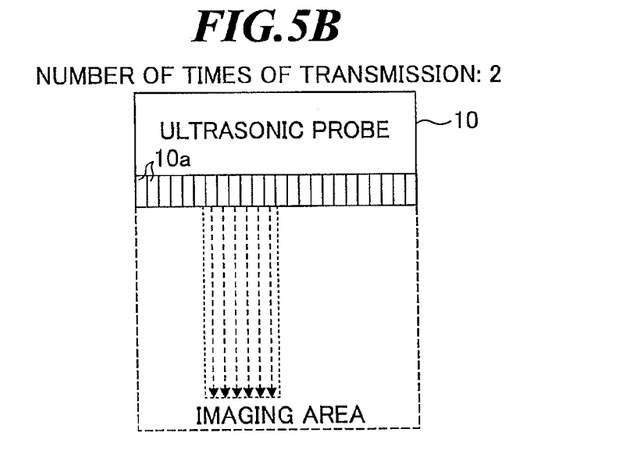
Figure 5C:
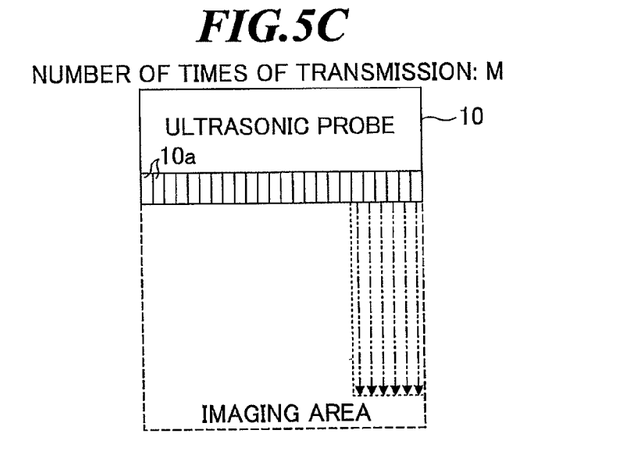

FIGS. 5A-5C are diagrams for explanation of transmission operation in a frame-sequential imaging mode. As shown in FIG. 5A, drive signals are supplied to a group of ultrasonic transducers selected from among the plural ultrasonic transducers 10a included in the ultrasonic probe 10, and the selected group of ultrasonic transducers simultaneously transmit ultrasonic waves. Here, it is desirable that phases of the ultrasonic waves to be simultaneously transmitted from the selected group of ultrasonic transducers are made the same.

As shown in FIG. 5B, a group of ultrasonic transducers for simultaneously transmitting ultrasonic waves are shifted plural by plural, and thereby, the object is scanned. That is, a center position of a group of ultrasonic transducers, which simultaneously transmits ultrasonic waves, is shifted by a distance not less than twice an interval of the plural ultrasonic transducers 10a. Here, the case is shown where the number of ultrasonic transducers for simultaneously transmitting ultrasonic waves and the number of ultrasonic transducers shifted at a time are equal to each other.

For example, given that the number of ultrasonic transducers 10a included in the ultrasonic probe 10 is $M \cdot N_G$ where M, $N_G$ are integral numbers equal to or more than "2", segmented areas obtained by dividing the imaging area into M areas are sequentially scanned by a group including $N_G$ ultrasonic transducers. Then, as shown in FIG. 5C, after the M times of transmission (M<N), scanning of the imaging area is completed. In the frame-sequential imaging mode, M segmented areas are scanned by M times of transmission operation in one frame period.

Figure 6:
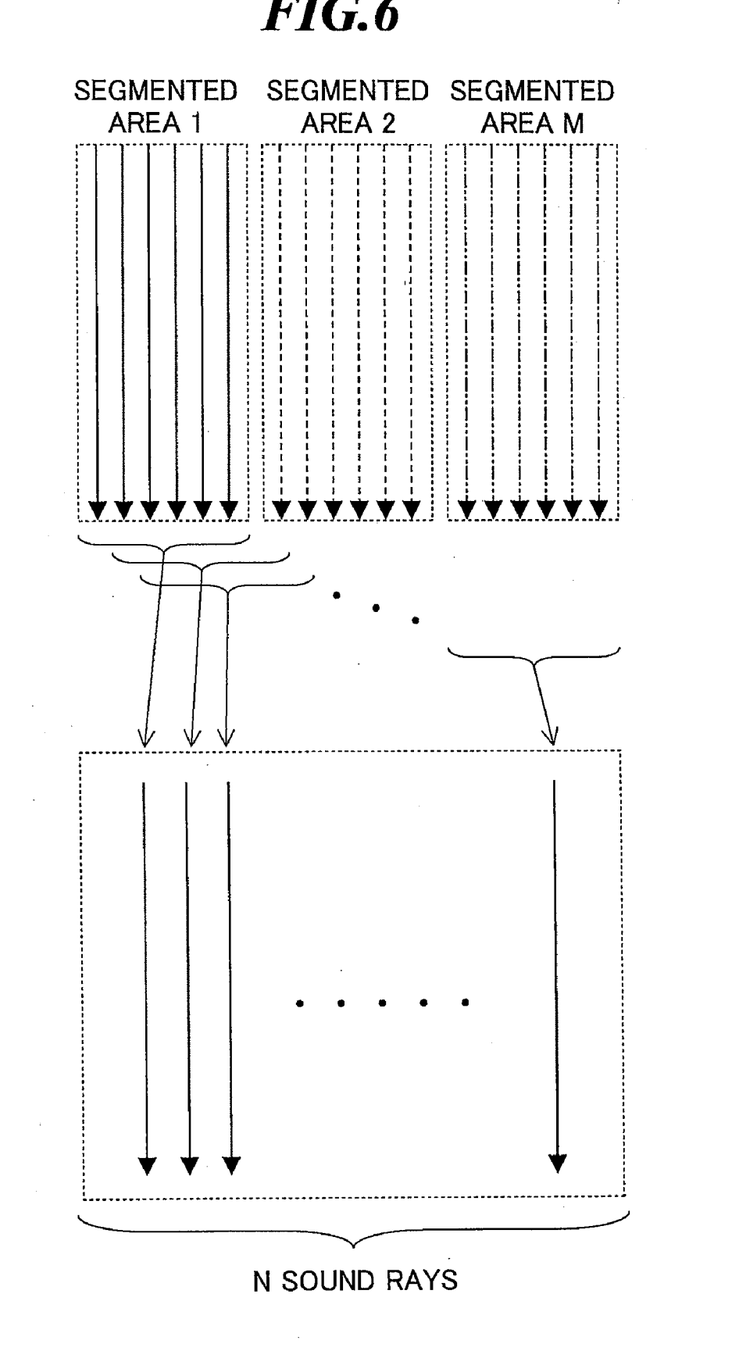
FIG. 6 is a diagram for explanation of a reception operation in the frame-sequential imaging mode.

FIG. 6 is a diagram for explanation of a reception operation in the frame-sequential imaging mode. In the frame-sequential imaging mode, delay times of the reception signals are corrected such that the reception signals obtained by the plural ultrasonic transducers receiving ultrasonic echoes generated in the M segmented areas become temporally continuous. As shown in FIG. 6, reception signals obtained by a selected group of ultrasonic transducers are phase-matched and added to one another, and thereby, a sound ray signal corresponding to one sound ray is obtained. By repeating this operation, sound ray signals corresponding to the N sound rays are obtained in one frame period.

In the frame-sequential imaging mode, transmission and reception of ultrasonic waves for each segmented area may be performed plural times in one frame period, and an SN ratio of the reception signals may be improved by adding or averaging the reception signals obtained plural times in one frame period from the same ultrasonic transducer. Here, assuming that a number of times of transmission of ultrasonic waves for each segmented area in one frame period is K, it is necessary that the relation M·K<N is established. Thereby, even if the number of times of transmission is increased, a frame rate higher than that in the line-sequential imaging mode is realized.

In this case, under the control of the scan control unit 11 as shown in FIG. 1, the transmission control unit 13 controls the drive signal generating unit 14 such that each of the $N_G$ ultrasonic transducers transmits ultrasonic waves plural times in one frame period. The reception signals sequentially obtained from each of the $N_G$ ultrasonic transducers are stored in the reception signal storage unit 24, and the calculation unit 23 performs calculation processing of one of addition and averaging (arithmetic mean or geometrical mean) of reception signals obtained plural times in one frame period from each ultrasonic transducer, and then, outputs calculation result to the B-mode image generating unit 30.

In the above explanation of the frame-sequential imaging mode, an example of performing transmission operation such that M segmented areas never overlap with each other. However, in a modified example of the frame-sequential imaging mode, transmission operation may be performed such that M segmented areas overlap with each other. The transmission operation is performed such that M segmented areas overlap with each other while shifting the $N_G$ ultrasonic transducers, which simultaneously transmit ultrasonic waves, $N_S$ by $N_S$ ($1<N_S<N_G$), and reception signals obtained plural times in one frame period from the same ultrasonic transducer are averaged so as to improve an SN ratio of the reception signals.

In this case, under the control of the scan control unit 11 as shown in FIG. 1, the transmission control unit 13 controls the drive signal generating unit 14 such that at least one ultrasonic transducer transmits ultrasonic waves to the overlapped portion of the segmented areas plural times in one frame period. The reception signals sequentially obtained from the at least one ultrasonic transducer are stored in the reception signal storage unit 24, and the calculation unit 23 performs calculation processing of one of addition and averaging (arithmetic mean or geometrical mean) of reception signals obtained plural times in one frame period from the at least one ultrasonic transducer, and then, outputs calculation result to the B-mode image generating unit 30. As to the ultrasonic transducer which transmits ultrasonic waves once in one frame period, the calculation unit 23 outputs reception signal obtained once in one frame period from the ultrasonic transducer to the B-mode image generating unit 30 without calculation.

Figure 7A:
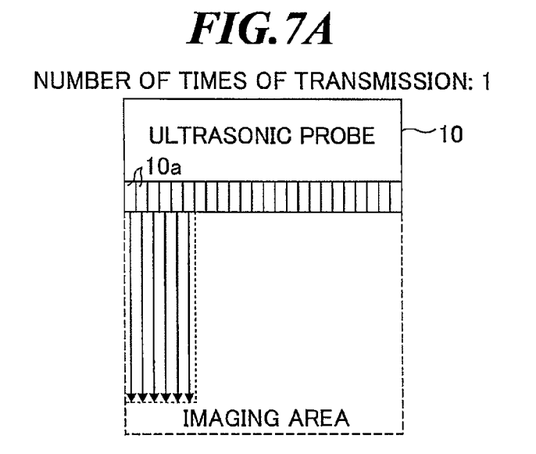
FIGS. 7A-7C are diagrams for explanation of transmission operation in a modified example of the frame-sequential imaging mode.
Figure 7B:
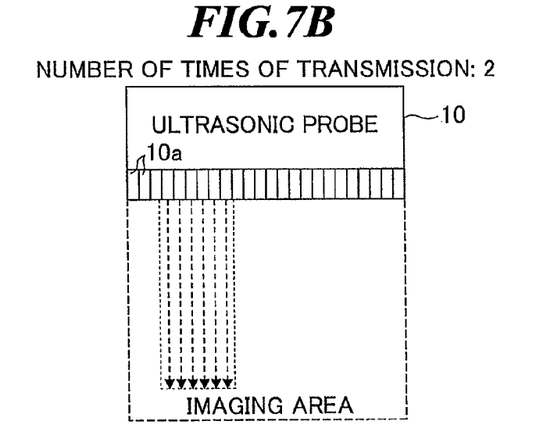
Figure 7C:
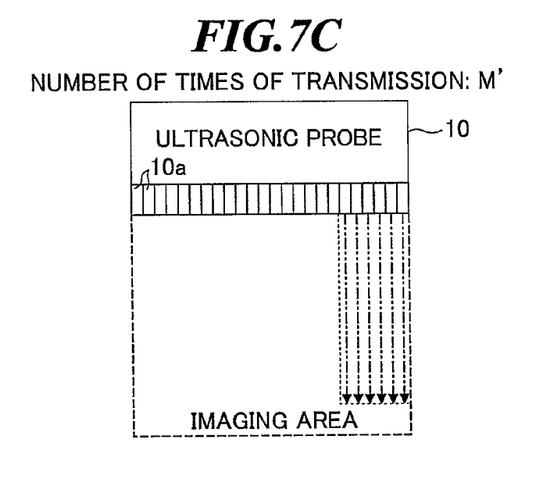

FIGS. 7A-7C are diagrams for explanation of transmission operation in the modified example of the frame-sequential imaging mode. As shown in FIG. 7A, drive signals are supplied to a group of ultrasonic transducers (six ultrasonic transducers in FIG. 7A) selected from among the plural ultrasonic transducers 10a included in the ultrasonic probe 10, and the selected group of ultrasonic transducers simultaneously transmit ultrasonic waves.

As shown in FIG. 7B, a group of ultrasonic transducers for simultaneously transmitting ultrasonic waves are shifted three by three, and thereby, the object is scanned. Then, as shown in FIG. 7C, after the M' times of transmission (M'=2M-1, for example), scanning of the imaging area is completed. In the modified example of the frame-sequential imaging mode, M segmented areas are scanned by M' times of transmission operation in one frame period. In the example as shown in FIGS. 7A-7C, although only once transmission is performed in one frame period for both ends of the imaging area, the both ends of the imaging area are apt to not be designated as a region of interest, and a little low SN ratio can be permitted.

Figure 8A:
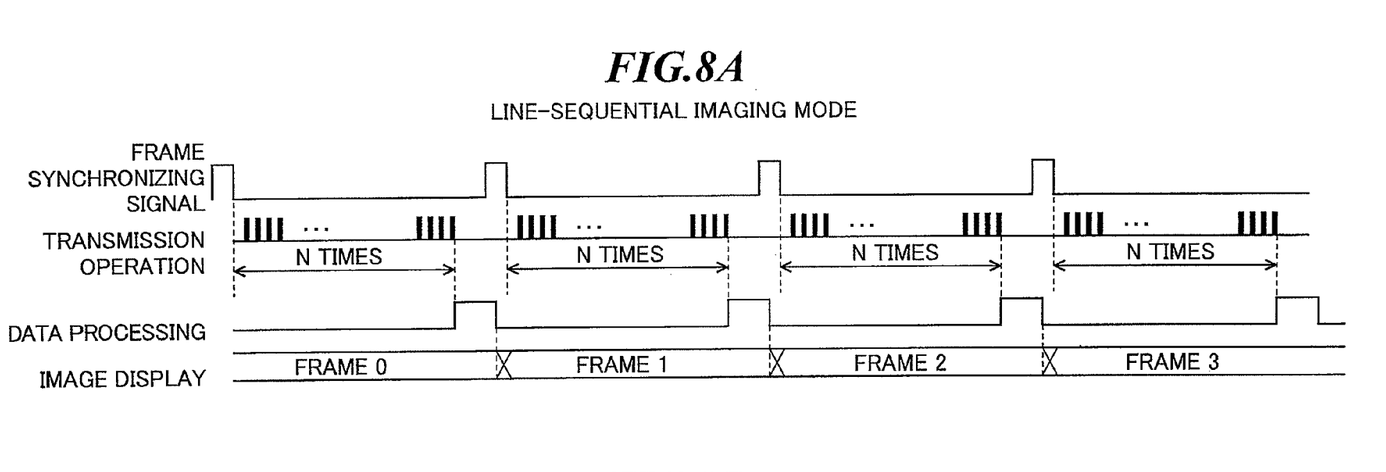
FIGS. 8A and 8B are diagrams for explanation of imaging operation in comparison between the line-sequential imaging mode and the frame-sequential imaging mode.
Figure 8B:
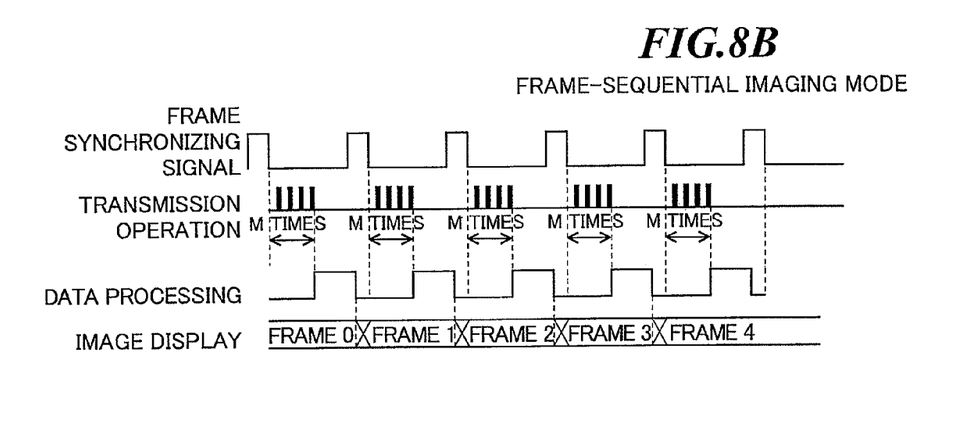

FIGS. 8A and 8B are diagrams for explanation of imaging operation in comparison between the line-sequential imaging mode and the frame-sequential imaging mode.

FIG. 8A shows imaging operation in the line-sequential imaging mode. In the line-sequential imaging mode, in one frame period represented by a frame synchronizing signal, N times of transmission operation are performed while shifting a group of ultrasonic transducers, which simultaneously transmit ultrasonic waves, one by one. After the transmission operation is completed, data processing for generating an image signal based on the reception signals is performed. As a result, images of frame 0, frame 1, frame 2, . . . are displayed in synchronization with the frame synchronizing signals.

In the line-sequential imaging mode, in the case where the imaging area is the same, the spatial resolution can be improved by increasing the times of transmission for one frame to increase the imaging line density. Therefore, the line-sequential imaging mode is useful in observation of abdomen and leg vein less affected by heart beat. On the other hand, the frame rate becomes lower because of the greater number of transmission for one frame.

FIG. 8B shows imaging operation in the frame-sequential imaging mode. In the frame-sequential imaging mode, in one frame period represented by a frame synchronizing signal, M times of transmission operation are performed while shifting a group of ultrasonic transducers, which simultaneously transmitting ultrasonic waves, plural by plural. After the transmission operation is completed, data processing for generating an image signal based on the reception signals is performed. As a result, images of frame 0, frame 1, frame 2, . . . are displayed in synchronization with the frame synchronizing signals.

In the frame-sequential imaging mode, in the case where the imaging area is the same, the time resolution can be improved because the frame period can be drastically shortened. Therefore, the frame-sequential imaging mode is useful in observation of parts assumed to quickly move as in an ultrasonic examination of heart. On the other hand, contrast resolution becomes lower because ultrasonic energy to be used for generating one image is small. However, the spatial resolution can be improved by increasing the times of transmission per unit time to increase the imaging line density, and thus, the frame-sequential imaging mode may be also useful in observation of abdomen and leg vein less affected by heartbeat.

The line-sequential imaging mode and the frame-sequential imaging mode can be switched by the operator pressing down the line-sequential/frame-sequential switching button 71a (FIG. 1) as explained above. However, the control unit 72 (FIG. 1) may automatically switch the modes as will be explained below.

The control unit 72 can set one of the line-sequential imaging mode and the frame-sequential imaging mode according to the predetermined setting depending on a part as an examination object. For example, the control unit 72 sets the frame-sequential imaging mode when the part as the examination object is heart, and sets the line-sequential imaging mode when the part as the examination object is abdomen. Thereby, the time resolution can be improved when the part as the examination object is heart, and the spatial resolution can be improved when the part as the examination object is abdomen.

Further, the control unit 72 can set one of the line-sequential imaging mode and the frame-sequential imaging mode according to the setting of a display depth. For example, the control unit 72 sets the line-sequential imaging mode when the set maximum display depth $D_{MAX}$ is equal to or less than a predetermined width D1, and sets the frame-sequential imaging mode when the set maximum display depth $D_{MAX}$ is more than the predetermined width D1. Thereby, the spatial resolution can be improved when a shallow region is displayed and the time resolution can be improved when a deep region is displayed.

Furthermore, the control unit 72 can set one of the line-sequential imaging mode and the frame-sequential imaging mode according to whether a difference ΔL between frames is larger than a predetermined value L1 or not with respect to plural pixel luminance values included in each frame (e.g., integration values or average values). For example, the control unit 72 sets the line-sequential imaging mode when the difference ΔL between frames is equal to or less than the predetermined value L1, and sets the frame-sequential imaging mode when the difference ΔL between frames is more than the predetermined value L1. Thereby, the spatial resolution can be improved when the motion of the object of imaging is in a small range and the time resolution can be improved when the motion of the object of imaging is in a wide range.

In addition, the operator can set the predetermined width D1 or the predetermined value L1 by operating the console 71.

The invention claimed is:

1. An ultrasonic diagnostic apparatus comprising:
an ultrasonic probe including plural ultrasonic transducers configured to transmit ultrasonic waves to an object to be inspected according to drive signals and receiving ultrasonic echoes propagating from the object to output reception signals;
a drive signal generating unit configured to supply the drive signals to said plural ultrasonic transducers, respectively;
a reception signal processing unit configured to process the reception signals outputted from said plural ultrasonic transducers, respectively;
a control unit configured to set one of a first imaging mode and a second imaging mode;
a transmission control unit configured to control said drive signal generating unit to scan the object while shifting a center position of a group of ultrasonic transducers, which simultaneously transmit ultrasonic waves, by a distance not larger than an interval of said plural ultrasonic transducers in said first imaging mode, and to control said drive signal generating unit to scan the object while shifting a center position of a group of ultrasonic transducers, which simultaneously transmit ultrasonic waves, by a distance not less than twice the interval of said plural ultrasonic transducers in said second imaging mode; and
an image generating unit configured (i) in said first imaging mode, to perform reception focusing processing on the reception signals outputted from said plural ultrasonic transducers and processed by said reception signal processing unit to obtain a number of sound ray signals in each frame period, and thereby generating an image signal at a first frame rate, and (ii) in said second imaging mode, to correct delay times of the reception signals outputted from said plural ultrasonic transducers and processed by said reception signal processing unit such that the reception signals become temporally continuous in each frame period, performing reception focusing processing on the reception signals to obtain the same number of sound ray signals in each frame period as that in said first imaging mode, and thereby generating an image signal at a second frame rate higher than said first frame rate.

2. The ultrasonic diagnostic apparatus according to claim 1, wherein:
said transmission control unit is configured to control said drive signal generating unit such that at least one ultrasonic transducer transmits ultrasonic waves plural times in one frame period in said second imaging mode; and
said reception signal processing unit is configured to perform calculation processing of one of addition and averaging of reception signals obtained plural times in one frame period from said at least one ultrasonic transducer in said second imaging mode, and then, outputs calculation result to said image generating unit.

3. The ultrasonic diagnostic apparatus according to claim 2, wherein said control unit is configured to set one of said first imaging mode and said second imaging mode according to predetermined setting depending on a part as an examination object.

4. The ultrasonic diagnostic apparatus according to claim 2, wherein said control unit is configured to set one of said first imaging mode and said second imaging mode according to setting of a display depth.

5. The ultrasonic diagnostic apparatus according to claim 2, wherein said control unit is configured to set one of said first imaging mode and said second imaging mode according to whether a difference between frames is larger than a predetermined value or not.

6. The ultrasonic diagnostic apparatus according to claim 5, wherein said predetermined value is set according to an operation by an operator.

7. The ultrasonic diagnostic apparatus according to claim 1, wherein said control unit is configured to set one of said first imaging mode and said second imaging mode according to predetermined setting depending on a part as an examination object.

8. The ultrasonic diagnostic apparatus according to claim 1, wherein said control unit is configured to set one of said first imaging mode and said second imaging mode according to setting of a display depth.

9. The ultrasonic diagnostic apparatus according to claim 1, wherein said control unit is configured to set one of said first imaging mode and said second imaging mode according to whether a difference between frames is larger than a predetermined value or not.

10. The ultrasonic diagnostic apparatus according to claim 9, wherein said predetermined value is set according to an operation by an operator.

11. The ultrasonic diagnostic apparatus according to claim 1, wherein said control unit is configured to store information on the imaging mode in connection with the image signal in response to a command for saving the image signal.

12. An ultrasonic imaging method to be used in an ultrasonic diagnostic apparatus having an ultrasonic probe including plural ultrasonic transducers configured to transmit ultrasonic waves to an object to be inspected according to drive signals and receive ultrasonic echoes propagating from the object to output reception signals, a drive signal generating unit configured to supply the drive signals to said plural ultrasonic transducers, respectively, and a reception signal processing unit configured to process the reception signals outputted from said plural ultrasonic transducers, respectively, said method comprising the steps of:
(a) setting one of a first imaging mode and a second imaging mode;
(b) controlling said drive signal generating unit in said first imaging mode to scan the object while shifting a center position of a group of ultrasonic transducers, which simultaneously transmit ultrasonic waves, by a distance not larger than an interval of said plural ultrasonic transducers, performing reception focusing processing on the reception signals outputted from said plural ultrasonic transducers and processed by said reception signal processing unit to obtain a number of sound ray signals in each frame period, and thereby generating an image signal at a first frame rate; and
(c) controlling said drive signal generating unit in said second imaging mode to scan the object while shifting a center position of a group of ultrasonic transducers, which simultaneously transmit ultrasonic waves, by a distance not less than twice the interval of said plural ultrasonic transducers, correcting delay times of the reception signals outputted from said plural ultrasonic transducers and processed by said reception signal processing unit such that the reception signals become temporally continuous in each frame period, performing reception focusing processing on the reception signals to obtain the same number of sound ray signals in each frame period as that in said first imaging mode, and thereby generating an image signal at a second frame rate higher than said first frame rate.

13. The ultrasonic imaging method according to claim 12, wherein step (c) includes controlling said drive signal generating unit such that at least one ultrasonic transducer transmits ultrasonic waves plural times in one frame period, performing calculation processing of one of addition and averaging of reception signals obtained plural times in one frame period from said at least one ultrasonic transducer, and then, generating the image signal.

14. The ultrasonic imaging method according to claim 13, wherein step (a) includes setting one of said first imaging mode and said second imaging mode according to predetermined setting depending on a part as an examination object.

15. The ultrasonic imaging method according to claim 13, wherein step (a) includes setting one of said first imaging mode and said second imaging mode according to setting of a display depth.

16. The ultrasonic imaging method according to claim 13, wherein step (a) includes setting one of said first imaging mode and said second imaging mode according to whether a difference between frames is larger than a predetermined value or not.

17. The ultrasonic imaging method according to claim 12, wherein step (a) includes setting one of said first imaging mode and said second imaging mode according to predetermined setting depending on a part as an examination object.

18. The ultrasonic imaging method according to claim 12, wherein step (a) includes setting one of said first imaging mode and said second imaging mode according to setting of a display depth.

19. The ultrasonic imaging method according to claim 12, wherein step (a) includes setting one of said first imaging mode and said second imaging mode according to whether a difference between frames is larger than a predetermined value or not.

20. An ultrasonic imaging program to be used in an ultrasonic diagnostic apparatus having an ultrasonic probe including plural ultrasonic transducers configured to transmit ultrasonic waves to an object to be inspected according to drive signals and receive ultrasonic echoes propagating from the object to output reception signals, a drive signal generating unit configured to supply the drive signals to said plural ultrasonic transducers, respectively, and a reception signal processing unit configured to process the reception signals outputted from said plural ultrasonic transducers, respectively, said program embodied in non-transitory form on a computer readable medium and allowing a CPU to execute the procedures of:

(a) setting one of a first imaging mode and a second imaging mode;

(b) controlling said drive signal generating unit in said first imaging mode to scan the object while shifting a center position of a group of ultrasonic transducers, which simultaneously transmit ultrasonic waves, by a distance not larger than an interval of said plural ultrasonic transducers, performing reception focusing processing on the reception signals outputted from said plural ultrasonic transducers and processed by said reception signal processing unit to obtain a number of sound ray signals in each frame period, and thereby generating an image signal at a first frame rate; and (c) controlling said drive signal generating unit in said second imaging mode to scan the object while shifting a center position of a group of ultrasonic transducers, which simultaneously transmit ultrasonic waves, by a distance not less than twice the interval of said plural ultrasonic transducers, correcting delay times of the reception signals outputted from said plural ultrasonic transducers and processed by said reception signal processing unit such that the reception signals become temporally continuous in each frame period, performing reception focusing processing on the reception signals to obtain the same number of sound ray signals in each frame period as that in said first imaging mode, and thereby generating an image signal at a second frame rate higher than said first frame rate.

21. The ultrasonic imaging program according to claim 20, wherein procedure (c) includes controlling said drive signal generating unit such that at least one ultrasonic transducer transmits ultrasonic waves plural times in one frame period, performing calculation processing of one of addition and averaging of reception signals obtained plural times in one frame period from said at least one ultrasonic transducer, and then, generating the image signal.

22. The ultrasonic imaging program according to claim 21, wherein procedure (a) includes setting one of said first imaging mode and said second imaging mode according to predetermined setting depending on a part as an examination object.

23. The ultrasonic imaging program according to claim 21, wherein procedure (a) includes setting one of said first imaging mode and said second imaging mode according to setting of a display depth.

24. The ultrasonic imaging program according to claim 21, wherein procedure (a) includes setting one of said first imaging mode and said second imaging mode according to whether a difference between frames is larger than a predetermined value or not.

25. The ultrasonic imaging program according to claim 20, wherein procedure (a) includes setting one of said first imaging mode and said second imaging mode according to predetermined setting depending on a part as an examination object.

26. The ultrasonic imaging program according to claim 20, wherein procedure (a) includes setting one of said first imaging mode and said second imaging mode according to setting of a display depth.

27. The ultrasonic imaging program according to claim 20, wherein procedure (a) includes setting one of said first imaging mode and said second imaging mode according to whether a difference between frames is larger than a predetermined value or not.

* * * * *